United States Patent
Yoo et al.

(10) Patent No.: US 9,125,920 B2
(45) Date of Patent: Sep. 8, 2015

(54) ANTIBACTERIAL SYNTHETIC FIBER AND MANUFACTURING METHOD THEREOF

(75) Inventors: In-Sik Yoo, Goyang-si (KR); Myung-Ho Seok, Seoul (KR)

(73) Assignees: Bong Chul Kim, Gunpo-si, Gyeonggi-do (KR); Sae Yol Yoo, Goyang-si, Gyeonggi-do (KR)

( * ) Notice: Subject to any disclaimer, the term of this patent is extended or adjusted under 35 U.S.C. 154(b) by 360 days.

(21) Appl. No.: 13/579,130

(22) PCT Filed: Feb. 1, 2012

(86) PCT No.: PCT/KR2012/000777
§ 371 (c)(1),
(2), (4) Date: Oct. 17, 2012

(87) PCT Pub. No.: WO2012/105810
PCT Pub. Date: Aug. 9, 2012

(65) Prior Publication Data
US 2013/0034620 A1 Feb. 7, 2013

(30) Foreign Application Priority Data

Feb. 1, 2011 (KR) .................. 10-2011-0010191
Jun. 13, 2011 (KR) .................. 10-2011-0056772

(51) Int. Cl.
| | | |
|---|---|---|
| A61K 36/00 | (2006.01) |
| A61K 36/82 | (2006.01) |
| A61K 36/15 | (2006.01) |
| A61K 36/16 | (2006.01) |
| A61K 36/54 | (2006.01) |
| A61K 36/14 | (2006.01) |
| A61K 36/63 | (2006.01) |
| A61K 36/73 | (2006.01) |
| B29C 47/00 | (2006.01) |
| D01F 1/10 | (2006.01) |
| D01F 6/06 | (2006.01) |
| D01F 6/62 | (2006.01) |

(52) U.S. Cl.
CPC ............... *A61K 36/63* (2013.01); *A61K 36/14* (2013.01); *A61K 36/15* (2013.01); *A61K 36/16* (2013.01); *A61K 36/73* (2013.01); *A61K 36/82* (2013.01); *B29C 47/0014* (2013.01); *D01F 1/103* (2013.01); *D01F 6/06* (2013.01); *D01F 6/62* (2013.01)

(58) Field of Classification Search
None
See application file for complete search history.

(56) References Cited

U.S. PATENT DOCUMENTS

| 2005/0170167 A1* | 8/2005 | Kim et al. .................. 428/313.3 |
| 2007/0031664 A1* | 2/2007 | Kuwano et al. ............... 428/364 |

FOREIGN PATENT DOCUMENTS

| JP | 2000-119914 A | 4/2000 |
| JP | 2008-255518 A | 10/2008 |
| KR | 10-2000-0058680 A | 10/2000 |
| KR | 20-0372999 Y1 | 1/2005 |
| KR | 10-0910241 B1 | 7/2009 |

OTHER PUBLICATIONS

International Search Report for corresponding International Application No. PCT/KR2012/000777.

* cited by examiner

*Primary Examiner* — Qiuwen Mi
(74) *Attorney, Agent, or Firm* — Egbert Law Offices, PLLC

(57) ABSTRACT

Disclosed are an antibacterial synthetic fiber, and a method for manufacturing the same, characterized in that one or more antibacterial plant extracts are mixed with a fiber-formable polymer and the mixture is melt spun at 200~300° C. The antibacterial synthetic fiber exhibits excellent and persistent antibacterial activity. In addition, the antibacterial synthetic fiber is superior in physical property to conventional antibacterial fibers and is suitable for use as a material for clothes.

8 Claims, 1 Drawing Sheet

PHOTO)
 Test Bacteria — *Staphylococcus aureus(MRSA)* ATCC 33591
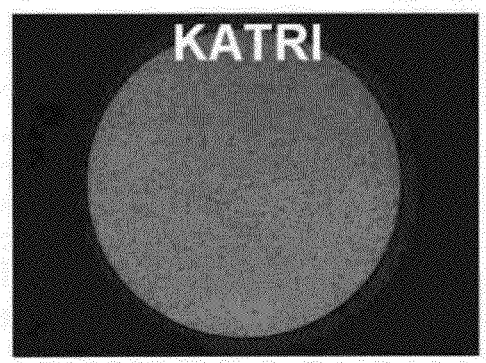 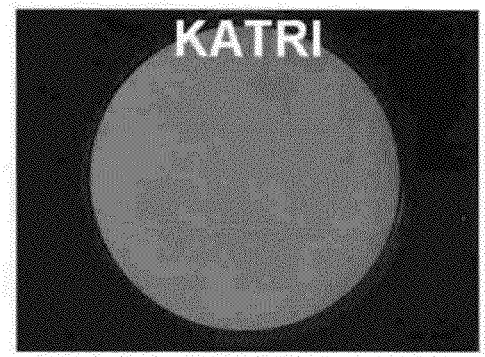
Control Sample, After 18h      Test Sample, After 18h / STAA11-3420

ANTIBACTERIAL SYNTHETIC FIBER AND MANUFACTURING METHOD THEREOF

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a method for manufacturing an antibacterial synthetic fiber. More particularly, the present invention relates to an antibacterial synthetic fiber comprising a plant extract, and a method for manufacturing the same.

2. Description of Related Art Including Information Disclosed Under 37 CFR 1.97 and 37 CFR 1.98.

A variety of attempts have been made to provide synthetic fibers with antibacterial activity. Prevalent among them is the inclusion of antibacterial inorganic substances into the synthetic fibers. Barleystone, jade, mica, and silver nanoparticles are representative of such inorganic substances. However, because they interfere with the manufacturing process of fibers, the inorganic substances are used in trace amounts which are not sufficient to guarantee the desired extent of antibacterial activity. Particularly, silver nanoparticles, known for their good antibacterial activity, additionally suffer from the drawback of having a negative influence on the light fastness of fibers following dyeing process, which is likely to cause a color change in the product.

In addition, conventional antibacterial synthetic fibers, although employing a trace amount of such an inorganic substance, are inferior in physical property to ordinary synthetic fibers.

In order to overcome these problems, extensive attention has been given to plant extracts or vegetable essential oils having antibacterial activity.

Exemplary are the disclosure of Korean Patent Nos. 10-0726409 and 10-0515808, which describe the direct coating and fixation of synthetic fibers with antibacterial plant extracts. The synthetic fibers coated with plant extracts do not persistently exhibit antibacterial activity because the extracts bleed out of the fibers upon washing.

The incorporation of plant extracts or vegetable essential oils into synthetic fibers arose as an alternative to coating, and methods therefor have been continuously studied.

As disclosed in Korean Patent Laid-Open Publication No. 2000-0058680 to the present inventors, efforts were made to elicit a deodorization effect by absorbing pyroligneous acid (wood vinegar) into porous mineral particles which were then used to prepare master batch chips. However, wood vinegar is viscous so that the mineral particles significantly aggregate when they are mixed with wood vinegar, resulting in plugging the filter of the mast batch facility. In addition, the aqueous liquid causes the degradation of the polymer, thus reducing the viscosity of the polymer. For these different reasons, the use of wood vinegar made it impossible to prepare master batch chips.

In the presence of water, mineral particles aggregate and once this aggregation of mineral particles has begun, it is fundamentally impossible to prevent. After a drying process, the aggregated mineral particles appear as solidified lumps which cannot be used in the manufacture of synthetic fibers. To be used, the aggregated mineral particles should be finely pulverized to the desired particle size, which may be achieved by repeating the milling process over time in, for example, a pin mill or a jet mill, followed by disintegration to prevent re-aggregation.

Although the mineral particles can be used after fine pulverization and disintegration, these processes are too expensive and increase the production cost.

Moreover, the fibers, even though obtained after the above-mentioned complex processes, still have the problem of having inferior physical properties because mineral substances act as a negative factor on physical properties as stated above.

Typical melting points for synthetic fibers are on the order of 200~300° C. at which plant extracts or vegetable oils, if used in advance of melt spinning, may undergo evaporation, degradation and/or denaturation and thus cannot be incorporated into fibers or will not exhibit sufficient functionally even if incorporated.

In an effort to solve this problem, Korean Patent No. 10-0910241 teaches an electrospinning method by which fine fibers can be drawn at low temperatures from a solution of (a) at least one component selected from among plant extracts and vegetable essential oils and (b) at least one fiber-formable polymer in (c) a solvent.

In electrospinning, a solution is erupted from a nozzle by the electrical force existing between a collector and the nozzle and becomes a jet stream which is then dried into nanofibers as the solvent evaporates when it reaches an incomplete region. Electrospinning is considered to be a solution to most of the problems associated with conventional spinning methods. However, electrospun fibers show poor mechanical properties because they are not accompanied by the strength enhancement imparted by the molecular orientation of the polymer. For this reason, electrospun fibers are not used for clothes, but are limited to special industrial purposes.

In addition, electrospinning further suffers from the disadvantage of its process being unstable, increasing the production cost, and having a low production yield.

The method disclosed in US 2010/0221969 A1 is suggested as a solution to these problems. In the method, microcapsules containing vegetable essential oils are mixed with a polymeric material prior to spinning so as to provide the fibers with perfume. However, the microcapsules degrade the physical properties of the fibers. Particularly, the vegetable essential oils entrapped within the microcapsules may be released under the high pressure and temperature conditions that the polymeric materials are put through until they are melted and spun upon melt spinning. In this case, the released oils may have a negative influence on the physical properties of the polymeric materials, thus incurring unbeneficial results in the manufacturing processes.

Technical Problem

It is an object of the present invention to provide an antibacterial synthetic fiber incorporated with an antibacterial plant extract.

It is another object of the present invention to provide a synthetic fiber with persistent antibacterial activity.

It is a further object of the present invention to provide a synthetic fiber with excellent antibacterial reproducibility.

It is still a further object of the present invention to provide an antibacterial synthetic fiber useful as a material for clothes.

BRIEF SUMMARY OF THE INVENTION

In accordance with an aspect thereof, the present invention provides a method for manufacturing a synthetic fiber, comprising: incorporating an extract of an antibacterial plant in an amount of from 0.01 to 10 wt % into a fiber-formable polymer: and melt-spinning the plant extract-incorporated polymer. Incorporating the antibacterial plant extract into the fiber-formable polymer may be carried out by (i) coating synthetic resin chips with the antibacterial plant extract and melt spinning the coated chips, (ii) preparing a master batch chip in the presence of the antibacterial plant extract and melt spinning the master batch chip alone or in combination with another typical synthetic chip, or (iii) adding the antibacterial plant extract during the polymerisation of the fiber-formable polymer.

A detailed description will be given of the present invention, infra. There are a variety of plants that have antibacterial activity. In fact, most plants exhibit antibacterial activity although its extent and kind differs from one species to another.

Illustrative examples of antibacterial plants are given below. It should be understood that so long as it has antibacterial activity, any plant, although not exemplified below, can be used in the present invention.

Extracts from the leaves, stems, flowers, fruits or seeds of plants belonging to Lauraceae, Cupressaceae, Pinaceae, Taxodiaceae, Araliaceae, Theaceae, Jumiperaceae, Rosaceae, Herbaceae, Oleaceae, Gingkoaceae, Caprifoliaceae, Linaceae, Poaceae, Rutaceae, Liliaceae, Nelumbonaceae, Lamiaceae, Asteraceae, Fagaceae, and Anacardiaceae, or sap from the plants are known to have excellent antibacterial activity.

In order to prevent the pyrolysis or thermal degradation of active gradients of these extracts, various methods including electrospinning have been suggested, as described above.

However, the present inventors found that active ingredients of the plant extracts are not thermally lyzed or degraded completely even during typical melt spinning. It is very useful when manufacturing antibacterial synthetic fibers for even a part of the active ingredients of plant extracts to remain antibacterially active after melt spinning in which they are thermally treated at the risk of pyrolysis or thermal degradation. This was revealed clearly in the present invention.

In the context of the present invention, the term "a part of the active ingredients remains antibacterially active" is intended to include "some of active ingredients exhibit full antibacterial activity" and "active ingredients lose their antibacterial activity to some degree." For example, after being dried for a long period of time at a high temperature and then undergoing a melt spinning process at high temperature and a dyeing process, the resulting fibers lack the characteristic fragrance of plants, hut exhibit antibacterial activity.

As used herein, the term "plant extract" means an extract produced when the leaves, flowers, stems, roots, fruits or seeds of a plant are boiled in water or an extract obtained by cooling and condensing the smoke generated when plants are heated.

The extract, whether obtained by boiling in water or condensing the smoke, is dried in a drying process or a master batch preparation process, so that the water is evaporated while the active ingredients remain within the fibers. Impurities such as solids are removed by filtration. The extract should be concentrated sufficiently. Concentration by heating may be continued until the weight of the extract reaches 25~60% of the total weight of the material (antibacterial plant) and water used, and more preferably 30~50%. For example, when the extract is insufficiently concentrated, a large content of combustible volatile matter is left, making it difficult to conduct the processes in series and degrading the physical properties of the fibers. On the other hand, an excessively concentrated extract increases the viscosity too much, leading to a decrease in workability. In addition, the excessive concentration may cause the degradation of the active ingredients. Extraction may be performed preferably at a temperature of 110~150° C. and more preferably at a temperature of 120~130° C. When the temperature used is too low, the extract is produced in an insufficient yield. On the other hand, no additional increase in extraction efficiency is obtained at a temperature exceeding the upper limit. In addition, high pressure is generated during extraction at too high of a temperature, increasing the risk of explosion.

The weight ratio of the material (antibacterial plant) to added water is on the order of 1:2~5, which is usually used for a decoction.

In the present invention, the plant extract in the form of a powder, which may be obtained by drying the liquid extract and pulverizing the dried residue or by drying and pulverizing the plant, cannot be used, not only because it is difficult to produce as fine a powder as desirable, but also because the powder is apt to undergo significant thermal degradation or burn during a pre-drying process or a melt spinning process. If the plant powder is burned, the synthetic resin rapidly decreases in viscosity, making spinning itself impossible.

The content of the plant extract in the fiber may be on the order of 0.01~10.0 wt %, preferably on the order of 0.05~6.0 wt %, and more preferably on the order of 0.1~3.0 wt %. At too low a content, only an insufficient effect is obtained from the plant extract. A content exceeding the upper limit does not guarantee additional effects, but has a negative influence on the physical properties of the fiber.

The method of the present invention comprises incorporating an extract of an antibacterial plant in an amount of from 0.01 to 10 wt %, preferably in an amount of 0.05~6.0 wt %, and more preferably in an amount of from 0.1 to 3.0 wt % into a fiber-formable polymer, and melt-spinning the plant extract-incorporated polymer.

Incorporation of the extract of the antibacterial plant into the fiber-formable polymer may be achieved using a coating method, a master batch method or a polymerisation method, as stated above.

In the coating method, preferably, a low temperature dryer or a rotary hot-air dryer is employed in order to prevent the degradation of the plant extract.

The synthetic fiber manufactured according to the method of the present invention comprises an antibacterial plant extract or wood vinegar in an amount of from 0.01 to 3.0 wt %, and exhibits excellent antibacterial activity with an inhibition rate of 90% or higher against bacteria at 18 hours after inoculation.

Advantageous Effects

As described hitherto, the antibacterial synthetic fibers of the present invention exhibit excellent and persistent antibacterial activity. Superior in physical property to conventional antibacterial fibers, the fibers of the present invention are also suitable for use in clothes, non-woven or industrial materials. In addition, their antibacterial activity is maintained after repetitive laundering, and shows therapeutic activity for dermal diseases and allergies, so that the fibers may be effectively used as materials of diapers for babies or patients. On the other hand, the fibers may be applied to antibacterial toothbrushes.

BRIEF DESCRIPTION OF THE DRAWINGS

FIG. 1 is a photograph showing a comparison of antibacterial activity between a test sample and a control 18 hours after inoculation.

DETAILED DESCRIPTION OF THE INVENTION

A better understanding of the present invention may be obtained through the following examples which are set forth to illustrate, but are not to be construed as limiting the present invention.

PREPARATION EXAMPLE 1

Preparation of Extract from *Forsythia Suspensa* Vahl

Four P.P. non-woven sacks, each containing 2 kg of pulverized powder of *Forsythia suspensa* Vahl, were put into a pressure decoction machine, and 20 kg of water was added. After boiling at 130° C. for 3 hours, the decoction was pressurised in a hydraulic linkage to produce 15 kg of an extract. This was concentrated into 5 kg by two rounds of filtration through a 5-micron filter.

The procedure was continued until 65 kg of a concentrated extract was obtained.

PREPARATION EXAMPLES 2 to 4

Preparation of Extracts from Lonicerae Flos, Ginkgo Leaves and Cinnamon Barks

Respective concentrated extracts from Lonicerae Flos, Ginkgo leaves, and cinnamon bark were prepared in a manner similar to that of Preparation Example 1.

PREPARATION EXAMPLES 5 to 8

Each of the extracts prepared in Preparation Examples 1 to 4 was mixed in an amount of 2 wt % with polypropylene chips, followed by drying at 60° C. for 2 hours in a rotary hot-air drier to afford coated chips.

Using a pilot spinning machine, 2 kg of the coating chips was spun at 225° C. in a typical manner to produce 150 denier/28 fila filaments.

PREPARATION EXAMPLE 9

The extract obtained in Preparation Example 1 was mixed in an amount of 3 wt % with nylon chips and dried at 60° C. for 3 hours in a rotary hot-air drier to afford 50 kg of coated chips. The coated chips were mixed at a ratio of 1:1 with general nylon chips and dried before spinning at 235° C. in a pilot spinning machine to produce 150 denier/28 fila nylon filaments.

PREPARATION EXAMPLE 10

Filtered quercus wood vinegar was mixed in an amount of 2 wt % with polypropylene chips and dried at 60° C. for 3 hours in a rotary hot-air drier to afford 50 kg of wood vinegar-coated chips. Two kilograms of the coated chips alone were spun at 225° C. in a typical manner to produce 150 denier/28 fila filaments.

PREPARATION EXAMPLE 11

65 Kg of the concentrated *Forsythia suspensa* Vahl extract prepared in Preparation Example 1 was mixed with 700 kg of polyester chips and dried before melt extrusion at 285° C. in a master batch extruder (twin screw, W&P, Germany) to produce 620 kg of master batch chips. The master batch chips were mixed at a weight ratio of 1:7 with typical polyester chips having an average intrinsic viscosity of 0.64 and spun to produce 4,080 kg of 1.4 D/38 mm staple fibers.

40 S/1 raw yarns (spun yarns) produced from the fibers were S/J knitted, and then subjected to scouring, dyeing and souping processes in a high-pressure dyeing machine, followed by treatment with a softener and a tentering process. A test sample was obtained using a general method.

EXAMPLES 1 to 8

The filaments prepared in Preparation Examples 5 to 10 were knitted into socks. These knitted goods and the test sample were assayed for antibacterial activity. Both were found to inhibit the growth of bacteria at a rate of 90% or higher 18 hours after inoculation thereinto, as shown in Table 1, below. The assay was conducted as follows.

Test method: KS K 0693-2006

The test sample prepared in Preparation Example 11 was also tested for antibacterial activity against superbacteria MRSA. The results are summarized in Table 2, below. The test was conducted under the following conditions. The test sample was photographed, together with a control, 18 hours after inoculation, as shown in FIG. 1.

Test Bacteria: *Staphylococcus aureus* (MRSA) ATCC 33591

Density of Inoculum: $1.2 \times 10^5$ CFU/mL CFU

Control: standard cotton fabric

Non-ionic surfactant: Tween80, added in an amount of 0.05% to the inoculum

TABLE 1

| Material | Bacteria | % Inhibition |
| --- | --- | --- |
| Preparation Example 5 (Forsythia suspensa Vahl) | *Staphylococcus aureus* ATCC. 6538 | ≥99.9% |
| | *Klebsiella pneumonia* ATCC 4352 | ≥99.9% |
| Preparation Example 6 (Lonicerae Flos) | *Staphylococcus aureus* ATCC 6538 | 99.7% |
| | *Klebsiella pneumonia* ATCC 4352 | 99.1% |
| Preparation Example 7 (Ginkgo leaves) | *Staphylococcus aureus* ATCC 6538 | 98.3% |
| | *Klebsiella pneumonia* ATCC 4352 | 92.1% |
| Preparation Example 8 (Cinnamon) | *Staphylococcus aureus* ATCC 6538 | ≥99.9% |
| | *Klebsiella pneumonia* ATCC 4352 | ≥99.9% |
| Preparation Example 9 (Forsythia suspensa Vahl) | *Staphylococcus aureus* ATCC 6538 | 99.4% |
| | *Klebsiella pneumonia* ATCC 4352 | ≥99.9% |
| Preparation Example 10 (Wood vinegar) | *Staphylococcus aureus* ATCC 6538 | ≥99.9% |
| | *Klebsiella pneumonia* ATCC 4352 | ≥99.9% |

TABLE 1-continued

| Material | Bacteria | % Inhibition |
|---|---|---|
| Preparation Example 11 (Forsythia suspensa Vahl) | Staphylococcus aureus ATCC 6538 | ≥99.99% |
| | Klebsiella pneumonia ATCC 4352 | ≥99.9% |
| | Staphylococcus aureus(MRSA) ATCC 33591 | ≥99.9% |

TABLE 2

Test Item — Test Result Sample 1
Antibacterial Activity: Tested according to KS K0693: 2006

| | Bacteria | | |
|---|---|---|---|
| | CFU/mL | No. of Bacteria | % Reduction |
| Early Stage (0 h) | 1,150 | 2.4E+04 | |
| | 1,220 | | |
| | 1,230 | | |
| Control (18 h) | 2,280,000 | 43E4+07 | |
| | 2,100,000 | | |
| | 2,090,000 | | |
| S# 1 (18 h) | 450 | 93 + 03 | 99.9% |
| | 500 | | |
| | 450 | | |

COMPARATIVE EXAMPLE 1

A single jersey fabric knitted from polyester 40 s/1 spun yarns was subjected to scouring, dyeing and souping processes in a high-pressure dyeing machine and then dewatered. The *Forsythia suspensa* Vahl extract was mixed in an amount of 5 wt % with softener-containing water (95 wt %), and the mixture was allowed to go through a mangle roller and subjected to a tenter process to afford a sample.

The sample showed an antibacterial activity of 99.9% before washing, but it was significantly decreased to 34% after five washes.

COMPARATIVE EXAMPLE 2

To 20 L of wood vinegar was added 5 kg of porous mineral particles. Upon the addition, the mineral particles aggregated. The wood vinegar-absorbed mineral particles were mixed in an amount of 2 wt % with polyester chips and dried at 130~160° C. for 6 hours. Thereafter, the aggregated mineral particles were solidified into lumps which could not be further processed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

We claim:

1. A method for manufacturing a synthetic fiber, the method comprising:
   incorporating an extract of an antibacterial plant in an amount from 0.01 to 10 wt % into a polyester chip, said extract being selected from an aqueous extract and wood vinegar: and
   melt-spinning the plant extract-incorporated polyester chip.

2. The method of claim 1, wherein the step of incorporating comprises coating the polyester chip with the extract in advance of the melt-spinning.

3. The method of claim 1, wherein the step of incorporating comprises mixing the extract with the polyester chip to afford a master batch chip.

4. The method of claim 1, wherein the step of incorporating comprises adding the extract to the polyester chip upon polymerization of the polyester chip.

5. The method of claim 1, wherein the plant extract-incorporated polyester chip is melt spun into a yarn for a nonwoven fabric.

6. The method of claim 1, wherein the antibacterial plant is selected from the group consisting of plants belonging to Lauraceae, Cupressaceae, Pinaceae, Taxodiaceae, Araliaceae, Theaceae, Juniperaceae, Rosaceae, Herbaceae, Oleaceae, Ginkgoaceae, Caprifoliaceae, Linaceae, Poaceae, Rutaceae, Liliaceae, Nelumbonaceae, Lamiaceae, Asteraceae, Fagaceae, and Anacardiaceae.

7. An antibacterial synthetic fiber, manufactured by the method of claim 1, wherein the extract of the antibacterial synthetic plant being in an amount of from 0.01 to 3.0 wt %.

8. The antibacterial synthetic fiber of claim 7, wherein the antibacterial synthetic fiber exhibiting an antibacterial rate of 90% 18 hours after inoculating bacteria into the fiber.

* * * * *